United States Patent
Xu et al.

(10) Patent No.: US 8,996,338 B2
(45) Date of Patent: Mar. 31, 2015

(54) METHOD OF COMPONENT CONCENTRATION DETECTION BASED ON REFERENCE WAVELENGTH

(75) Inventors: Kexin Xu, Tianjin (CN); Wenliang Chen, Tianjin (CN)

(73) Assignee: Tianjin Sunrise Technologies Development Co., Ltd., Tianjin (CN)

( * ) Notice: Subject to any disclaimer, the term of this patent is extended or adjusted under 35 U.S.C. 154(b) by 1120 days.

(21) Appl. No.: 12/996,089

(22) PCT Filed: Jun. 3, 2009

(86) PCT No.: PCT/CN2009/072113
§ 371 (c)(1),
(2), (4) Date: Feb. 11, 2011

(87) PCT Pub. No.: WO2009/146651
PCT Pub. Date: Dec. 10, 2009

(65) Prior Publication Data
US 2011/0131021 A1    Jun. 2, 2011

(30) Foreign Application Priority Data
Jun. 6, 2008    (CN) .......................... 2008 1 0053456

(51) Int. Cl.
G06F 17/10    (2006.01)
G01N 15/02    (2006.01)
G01N 21/359    (2014.01)
A61B 5/145    (2006.01)

(52) U.S. Cl.
CPC ........... *G01N 21/359* (2013.01); *A61B 5/14532* (2013.01)
USPC ............................................. 703/2; 356/336

(58) Field of Classification Search
CPC ................................................ G01N 21/359
USPC .............................................. 600/316; 703/2
See application file for complete search history.

(56) References Cited

U.S. PATENT DOCUMENTS 3,621,243 A * 11/1971 Olivier et al. ................... 378/51
4,655,225 A * 4/1987 Dahne et al. .................. 600/316
(Continued)

FOREIGN PATENT DOCUMENTS

| CN | 1699973 A | 11/2005 |
|---|---|---|
| CN | 101292875 A | 10/2008 |
| JP | 2004-150984 A | 5/2004 |

OTHER PUBLICATIONS

Applying the reference-wavelength method to improve the precision of glucose measurement by near infrared spectroscopy by Wenliang Chen et al; Chinese Optics Letters / vol. 5, No. 12 / Dec. 10, 2007; pp. 706-708.*

(Continued)

*Primary Examiner* — Akash Saxena
(74) *Attorney, Agent, or Firm* — Merchant & Gould P.C.

(57) ABSTRACT

A method of detecting a concentration of a target component by using a reference wavelength includes: defining a wavelength at which a light intensity is insensitive to the variation of the target component concentration as a reference wavelength for the target component; detecting spectra at both the reference wavelength and a further measuring wavelength; processing the spectrum detected at the further measuring wavelength, with the spectrum detected at the reference wavelength as an inner reference, to obtain a characteristic spectrum including specific information of the target component; building a calibration model between the characteristic spectrum and the concentration of the target component; and determining the concentration of the target component based on the calibration model.

5 Claims, 5 Drawing Sheets

(56) References Cited

U.S. PATENT DOCUMENTS

| | | | |
|---|---|---|---|
| 4,890,480 A * | 1/1990 | Young | 73/32 A |
| 5,070,874 A * | 12/1991 | Barnes et al. | 600/316 |
| 5,551,422 A * | 9/1996 | Simonsen et al. | 600/322 |
| 5,576,827 A * | 11/1996 | Strickland et al. | 356/336 |
| 6,044,285 A * | 3/2000 | Chaiken et al. | 600/316 |
| 6,289,230 B1 * | 9/2001 | Chaiken et al. | 600/322 |
| 6,343,507 B1 * | 2/2002 | Felling et al. | 73/152.19 |
| 6,377,828 B1 * | 4/2002 | Chaiken et al. | 600/316 |
| 6,643,020 B2 * | 11/2003 | Mizushima et al. | 356/432 |
| 7,009,180 B2 * | 3/2006 | Sterling et al. | 250/339.12 |
| 7,620,674 B2 * | 11/2009 | Ruchti et al. | 708/400 |
| 7,767,969 B2 * | 8/2010 | Nagai et al. | 250/340 |
| 8,239,139 B2 * | 8/2012 | Mycek et al. | 702/19 |
| 8,244,498 B2 * | 8/2012 | Wold et al. | 702/179 |
| 8,620,051 B2 * | 12/2013 | Djerizi et al. | 382/131 |
| 2001/0021803 A1 * | 9/2001 | Blank et al. | 600/322 |
| 2004/0019283 A1 * | 1/2004 | Lambert et al. | 600/476 |
| 2004/0068163 A1 * | 4/2004 | Ruchti et al. | 600/316 |
| 2005/0149300 A1 * | 7/2005 | Ruchti et al. | 703/2 |
| 2006/0017923 A1 * | 1/2006 | Ruchti et al. | 356/326 |
| 2006/0063987 A1 * | 3/2006 | Ota et al. | 600/310 |
| 2006/0094941 A1 * | 5/2006 | Cho et al. | 600/316 |
| 2009/0044636 A1 * | 2/2009 | Hope | 73/861.28 |
| 2009/0093977 A1 * | 4/2009 | Hauptmann et al. | 702/54 |
| 2011/0131021 A1 * | 6/2011 | Xu et al. | 703/2 |

OTHER PUBLICATIONS

Net analyte signal calculation for multivariate calibration—Joan Ferre et al Chemometrics and Intelligent Laboratory Systems 69 (2003) pp. 123-136.*

Luo, Y. et al. "Application of fiducial wavelength method in processing spectra of turbid media", Spectroscopy and Spectral Analysis, vol. 26, No. 8, Aug. 2006, pp. 1416-1418. English Abstract included.

Liu, Rong et al. "Influence of temperature change on the noninvasive blood glucose sensing by near-infrared spectroscopy", Journal of Tianjin University, vol. 41, No. 1, Jan. 2008, pp. 1-6. English Abstract included.

* cited by examiner

METHOD OF COMPONENT CONCENTRATION DETECTION BASED ON REFERENCE WAVELENGTH

This application is a National Stage Application of PCT/CN2009/072113, filed 3 Jun. 2009, which claims benefit of Serial No. 200810053456.9, filed 6 Jun. 2008 in China and which application are incorporated herein by reference. To the extent appropriate, a claim of priority is made to each of the above disclosed applications.

FIELD OF THE INVENTION

The present invention relates to a method of detecting concentrations of various components by near-infrared spectroscopy.

BACKGROUND OF THE INVENTION

The near-infrared (NIR) spectroscopy method, based on the near-infrared absorption spectra and the chemometrics technology, is mainly used for component sensing in human body (such as concentration of blood glucose). In the near-infrared region, the body fluid and soft tissue are relatively transparent and thus the light has a strong penetrability. In addition, the sensitivity, precision and reliability of quantitative analysis by the NIR spectroscopy method are significantly improved along with the great development of the chemometrics method and its applications in the near-infrared spectroscopy technology. The NIR spectroscopy method is recognized as the most promising technology for non-invasive detection in human body. An existing successful example is the non-invasive sensing of the blood oxygen saturation.

Figure 1:
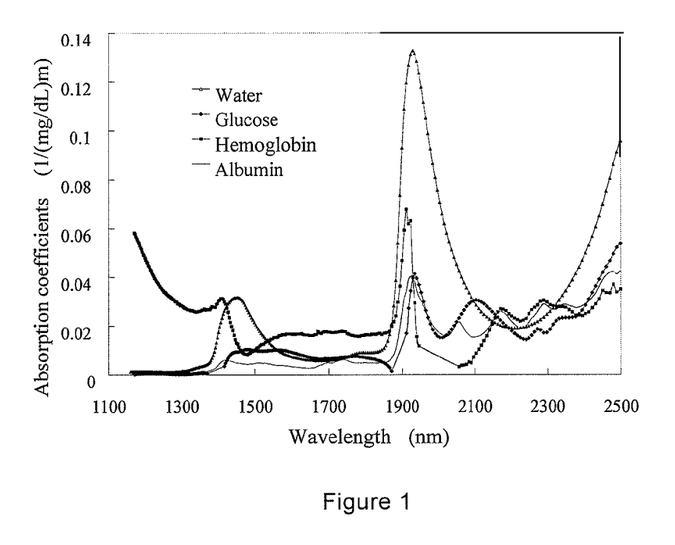
FIG. 1 is a graph showing near-infrared absorption spectra of different components in the blood.

The near-infrared spectrum (with a wavelength ranging from 780 to 2500 nm) is caused by a double-frequency or combined-frequency absorption of vibration at a fundamental-frequency in the mid-infrared region of different compounds which contain chemical bonds such as C—H, O—H or N—H. The characteristics of the near-infrared spectra will change with the concentrations of organic compounds containing the chemical bond —H or its relative combined inorganic compounds. Thus, the concentration variation of the target component could be analyzed based on the spectrum feature. However, the near-infrared spectra of different components in the blood or tissue fluid overlap with each other to a great extent, as shown in FIG. 1. The process of spectrum detection is greatly influenced by the instrument drifts, temperature variations and background noises. Therefore, a high detection precision is difficult to acquire according to the calibration model built by the data measured at a single wavelength.

Figure 2:
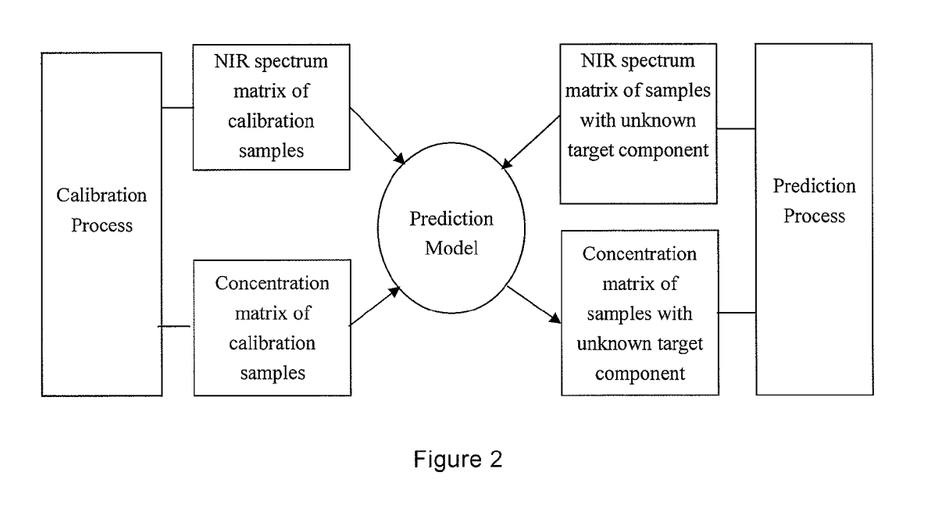
FIG. 2 is a block diagram showing the concept of quantitative analysis by the near-infrared spectroscopy.
Figure 3:
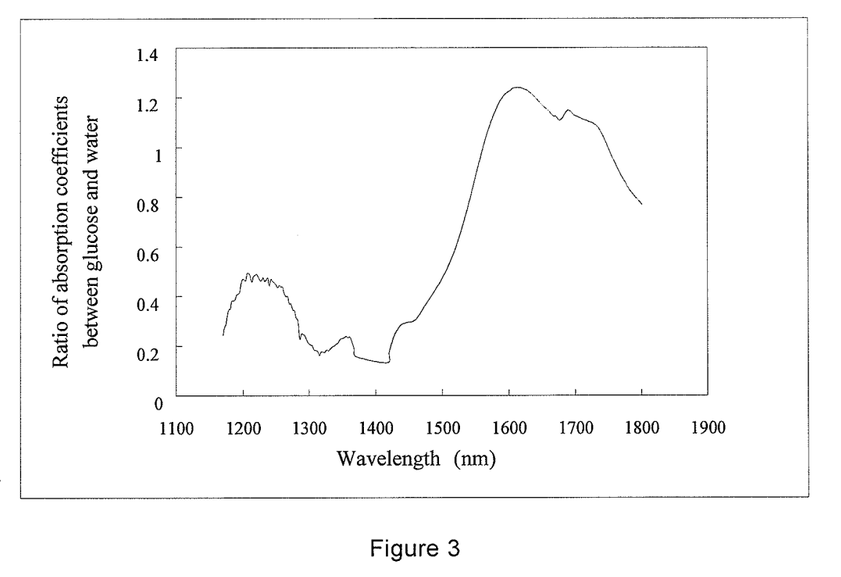
FIG. 3 is a graph showing a ratio of absorption coefficients between glucose and water.

The near-infrared spectroscopy, combined with the multi-variable analysis, is usually used for the qualitative detecting of material compositions, as shown in FIG. 2. Specifically, first, a series of calibration samples are designed to respectively have target component concentrations varied in a same interval, and then their near-infrared spectra are measured respectively. Next, the spectrum matrix and the concentration matrix of the samples are analyzed with the multivariable regression technology, and the calibration model is built to get the regression coefficient. Then, the near-infrared spectrum of the target sample with an unknown target component concentration is measured, and the spectrum matrix is analyzed and the concentration of the target component is conversely calculated based on the regression coefficient of the calibration model. As a most effective method, the PLS (Partial Least Square) is widely used for multivariable model calibration in the near-infrared spectroscopy analysis at present.

Though the near-infrared spectroscopy is one of the best methods to realize non-invasive sensing in human body, it is so complicated. Taking non-invasive blood glucose sensing as an example, the nonlinear scattering, which occurs when the near-infrared light passes through the dynamic changed tissue due to the complicated optical properties in the tissue, makes the glucose signal collection so difficult. In additional, the spectral signal caused by the variation of the blood glucose is very weak because of the small quantity of the blood glucose, and the absorption of the glucose itself overlaps the absorption of other components very badly. The strong absorption of water, protein and fattiness as well as the variation of body temperature and changes of other physiological conditions is the main interference factor. The key point of non-invasive blood glucose sensing by NIR is to collect the weak signal characterizing the variation of the glucose concentration from the badly overlapped backgrounds, which is influenced by various physiological factors.

SUMMARY OF THE INVENTION

In view of the above difficulties caused by overlapped absorption spectra, complicated background noises and the poor specificity of body components such as blood glucose in the non-invasive sensing of human body by the NIR spectroscopy, it is an object of the present invention to provide a method of detecting component concentration based on a reference wavelength. According to embodiments of the invention, the floating-reference measurement is achieved by determining an inner reference for the human body measurement. That is to say, a wavelength in the near-infrared light range, where the intensity of a probe light is most insensitive to the change of a target component concentration, is selected as the reference wavelength. The intensity variation of the light at the reference wavelength is used to evaluate the variation of light intensity caused by interference factors, in order to enhance the signal specificity of human components such as blood glucose and improve the measurement accuracy.

According to an aspect of the invention, there is provided a method for measuring a concentration of a target component by means of a reference wavelength. First, the reference wavelength for the target component is determined by theory deduction or experiments, and spectra at both the reference wavelength and a further measuring wavelength are detected. Next, a differential process is performed on the spectral signals at the further measuring wavelength with respect to the spectral signals at the reference wavelength as an inner reference, and the characteristic spectrum including information on the target component is collected. Then, the concentration of the target component could be predicted according to a mathematical calibration model for the characteristic spectrum. The light intensity variation measured at the reference wavelength contains all the variations caused by the interference factors other than the target component and is independent of the target component, and thus could be used as an inner reference in the human components sensing.

Further, according to various embodiments of the invention, there are provided methods of determining the reference wavelength theoretically or experimentally.

Specifically, the reference wavelength for the target component may be determined theoretically as follows. According to the volume replacement principle between the target component and the water or other solvent, the influence of the concentration variation of the target component on the absorption and scattering coefficients of the sample is calculated, in order to deduct and simulate the relation between the spectral variation and the concentration variation. A wavelength where the variation of the light intensity due to the concentration variation is zero is defined as the reference wavelength.

Alternatively, the reference wavelength for the target component may be determined experimentally as follows. The concentration of the target component in the sample is changed and corresponding spectra are measured, in order to get differential spectral graphs among various concentrations. The variation of light intensity is insensitive to the target component concentration when the differential spectral graph intersects the zero value. A wavelength corresponding to the zero value is defined as the reference wavelength for the target component.

Preferably, the characteristic signal of the target component may be extracted based on the reference wavelength. For a pure absorption sample, the characteristic signal including information on the concentration of the target component could be expressed as:

$$A_G(\lambda) = -\text{Ln}\left(\frac{I_s(\lambda)}{I_b(\lambda)} \cdot \frac{I_b(\lambda_r)}{I_s(\lambda_r)}\right).$$

For a complicated scattering sample, the characteristic signal including information on the concentration of the target component could be expressed as:

$$A_G(\lambda) = \text{Ln}\frac{I_b(\lambda) \cdot I_s(\lambda_r)}{I_s(\lambda) \cdot I_b(\lambda_r)} + K_{\Delta c} \cdot \text{Ln}\left(\frac{I_b(\lambda)}{I_b(\lambda_r)} \cdot \frac{I_0(t_b, \lambda_r)}{I_0(t_b, \lambda)}\right).$$

Here, $I_s(\lambda_r)$ and $I_b(\lambda_r)$ are intensities of the transmitted light from the target sample and the background sample at the reference wavelength respectively; $I_s(\lambda)$ and $I_b(\lambda)$ are intensities of the transmitted light from the target sample and the background sample at the measuring wavelength in the near-infrared band respectively; $I_0(t_b,\lambda_r)$ and $I_0(t_b,\lambda)$ are intensities of the light incident to the background sample at the reference wavelength and the measuring wavelength respectively; and $K_{\Delta c}$ is a percentage coefficient of the light path length variation caused by the concentration change of the target component of $\Delta c$.

According to various embodiments of the invention, the sample spectrum may be temperature corrected based on the reference wavelength. A difference spectral signal between two samples is defined as a sum signal of a difference signal induced by the temperature variation and a difference signal induced by the concentration variation of the target component. At the reference wavelength for the target component, the value of the difference signal induced by the concentration variation of the target component is equal to zero. According to the difference signal of light intensity at the reference wavelength, the temperature variation when measuring the samples is calculated, and thus the actual temperature of the sample is gained. The light intensity at the further measuring wavelength is temperature corrected, to get the measured spectrum corresponding to the temperature condition of the calibration model, in order to improve the measurement accuracy.

Based on the characteristic spectral matrix and the relative concentration matrix of the target component in a calibration set of samples, the calibration model could be built by the PLS (Partial Least Squares) method or the net analyte signal method, in order to predict the concentration of the target component by analyzing the spectra of a prediction set of samples.

The reference wavelength based measurement method proposed hereby can be applied to non-invasive or mini-invasive blood glucose sensing in human body for improving the measurement accuracy.

The near-infrared light range which is used in the non-invasive blood glucose sensing technology based on the reference wavelength proposed hereby is from 780 nm to 2500 nm.

In the reference wavelength method, the reference wavelength for the target component is only related to the characteristics of the target component itself and solvents such as water, but will not change with temperature.

According to embodiments of the present invention, a wavelength where the transmission intensity is insensitive to the variation of the target component is defined as the reference wavelength. During the measurement process, the light intensity or the absorbance value detected at the reference wavelength is supposed as the floating reference which does not change with the concentration of the target component. Therefore, the reference reflects the variation induced by other interference factors than the target component more effectively than the prior art. On this basis, the spectral signals at the further measuring wavelength is subjected to the differential process with respect to the light intensity or absorption information at the reference wavelength, in order to eliminate the interference induced by the factors besides the target component. Thus, it is possible to maximize the weak component information and improve the detecting accuracy of the weak component concentration in human body such as blood glucose.

DESCRIPTION OF THE PREFERRED EMBODIMENTS

To effectively cancel interferences in the near-infrared spectral measurement caused by other factors than the target component and thus to improve the measurement accuracy and sensitivity, there is provided a method of detecting concentration by using a reference wavelength. According to the characteristics of near-infrared absorption spectra of samples with a tested composition of different concentrations, the reference wavelength for the composition is defined. Then, based on signal changes at the reference wavelength, data process is done in the whole band by using the reference wavelength method to obtain a characterizing spectral signal of the tested composition. Further, a calibration model between the matrix of the characterizing spectral signal and that of the concentrations of the tested composition is established, to finally determine the concentration of the tested composition.

Acquisition of Reference Wavelength for Tested Composition

First, it is necessary to prove and obtain the existence characteristic of the reference wavelength and to obtain respective values of the reference wavelength for different tested compositions. Based on this, a relevant data preprocess model can be established to effectively extract the concentration signal. There are provided a method of theoretically deriving the reference wavelength and a method of obtaining it through experiments.

In the theoretical derivation, the influence of the concentration change of a tested composition on the absorption and scattering coefficient of the sample is calculated according to the theory of volume replacement between the tested composition and the water or other solvents, then the relationship between the spectrum and the concentration is derived or simulated, wherein a wavelength at which the light intensity is independent of the concentration of the tested composition is defined as the reference wavelength. Here, the existence characteristic of the reference wavelength is theoretically calculated and proved.

First, the existence characteristic of the reference wavelength for the pure absorption sample is analyzed. For the aqueous glucose solution, the increasing of the glucose concentration on one hand results in the rising of the intrinsic absorption of the glucose, and on the other hand leads to the reduction of the water concentration and thus the reduction of the intrinsic absorption of the water because more water is replaced by the glucose. Thus, the absorbance of the aqueous glucose solution and the pure water are given respectively by:

$$A_b = \alpha_w \cdot c_w \cdot l \quad (1)$$

$$A_s = (\alpha_w \cdot c_w + \alpha_g \cdot \Delta c_g + \alpha_w \cdot \Delta c_w) \cdot l \quad (2)$$

where $A_b$ and $A_s$ are the absorbance of the pure water as the background and the aqueous glucose solution, $c_w$ is the concentration of the pure water, $\Delta c_g$ is the concentration change of the glucose in the sample, $\Delta c_w$ is the resultant concentration change of the water due to the concentration change $\Delta c_g$ of the glucose, and $\alpha_w$ and $\alpha_g$ are the absorption coefficients of the water molecule and the glucose molecule respectively, whose wavelength characteristics are shown in FIG. 1.

A differential process is done between the absorbance of the sample and the background. When the measurement environment is same for the sample and the background, the characteristic signal of the glucose concentration change $A_G$ is given by:

$$A_G = A_s - A_b = (\alpha_g \cdot \Delta c_g + \alpha_w \cdot \Delta c_w) \cdot l \quad (3)$$

The absorbance of the sample is independent of the glucose concentration change at the reference wavelength for the glucose, that is, $A_G = 0$. According to equation (3), this means:

$$\alpha_g \cdot \Delta c_g + \alpha_w \cdot \Delta c_w = 0 \quad (4)$$

According to existing researches, the molar concentration of the pure water at 20° C. is $C_w^0 = 55.4M$, and if the glucose concentration raises by 1 mM, the molar concentration of the pure water will decrease by 0.0111%. The following equation is obtained according to equation (4):

$$\frac{\alpha_g}{\alpha_w} = -\frac{\Delta c_w}{\Delta c_g} \quad (5)$$
$$= 0.6217$$

That is, when the absorbance ratio of the glucose to the pure water is 0.6217, the corresponding wavelength is the reference wavelength for the glucose measurement. According to FIG. 4, the absorbance ratio of the glucose to the pure water reaches 0.6217 almost at the wavelength of 1525 nm. Therefore, the reference wavelength for the glucose measurement is 1525 nm.

For the complex scattering samples like human body, the absorption and scattering coefficients will change as the glucose concentration changes, which in combination result in the change in the light intensity. Therefore, the reference wavelength is one at which cancellation of effects of absorption and scattering happens.

$$\Delta I_S(\lambda, \Delta c_g) = \left( \frac{\partial I(\lambda)}{\partial \mu_a} \cdot \frac{\partial \mu_a}{\partial c_g} + \frac{\partial I(\lambda)}{\partial \mu_s'} \cdot \frac{\partial \mu_s'}{\partial c_g} \right) \Delta c_g = 0 \quad (6)$$

A series of equations are derived according to our previous efforts:

$$\frac{\partial I(\lambda)}{\partial \mu_a} = -\frac{I_0(\lambda) \cdot l}{\exp\left\{ l \cdot \left[ \mu_a(\lambda) + \frac{\mu_s'(\lambda)}{1 - g(\lambda)} \right] \right\}} \quad (7)$$

$$\frac{\partial I(\lambda)}{\partial \mu_s'} = \frac{I_0(\lambda) \cdot l}{[g(\lambda) - 1] \cdot \exp\left\{ l \cdot \left[ \mu_a(\lambda) + \frac{\mu_s'(\lambda)}{1 - g(\lambda)} \right] \right\}} \quad (8)$$

$$\frac{\partial \mu_a}{\partial c_g} = \alpha_g(\lambda) - 0.6217 \cdot \alpha_w(\lambda) \quad (9)$$

$$\frac{\partial \mu_s'}{\partial c} = -\frac{6.44 * 10^{-5} * r^{2.37} * \rho_s * n_s * (n_s - n_w)^{1.09}}{\lambda^{0.37} * n_w^{3.09}} \quad (10)$$

where $I(\lambda)$ and $I_0(\lambda)$ are the input and output light intensities respectively, $\mu_a$ and $\mu_s'$ are the absorption and scattering coefficients of the scattering sample respectively, g is the anisotropic factor of the scattering sample, l is the path length of the output light passing through the sample, $n_s$ is the refractive index of the scattering particles in the sample, $n_w$ is the refractive index of the water, r is the radius of the scattering particles, and $\rho_s$ is the number of the scattering particles per unit volume ($nm^{-3}$).

According to equations (6) to (10), the condition for the existence of the reference wavelength $\lambda_r$ of the scattering sample is given by:

$$\frac{6.44*10^{-5}*r^{2.37}*\rho_s*n_s*(n_s-n_w)^{1.09}}{\lambda_r^{0.37}*n_w^{3.09}}*\frac{1}{1-g(\lambda_r)}= \qquad (11)$$

$$\alpha_g(\lambda_r)-0.6217\cdot\alpha_w(\lambda_r)$$

The above derivation needs accurate molar absorption coefficients of the respective compositions as well as the replacement relations among the respective composition in the sample. For more complex samples, there is provided a method of determining the reference wavelength through experiments.

The procedures of the experiment-based method are as follows:

1. Measuring the spectra under different concentrations of the tested composition $I_{s1}(\lambda)$, $I_{s2}(\lambda)$, $I_{s3}(\lambda)$, ... and also the spectra of corresponding background samples with zero concentration of the tested composition $I_{b1}(\lambda)$, $I_{b2}(\lambda)$, $I_{b3}(\lambda)$, ...;
2. Calculating the differential spectra of the tested composition with different concentrations, i.e. the characteristic spectral signals containing the information of concentrations of the tested composition, through a differential process on the light intensity between the tested samples and the background samples $A_{concentration1}(\lambda)$, $A_{concentration2}(\lambda)$, $A_{concentration3}(\lambda)$, ...; and
3. Analyzing the differential spectral characteristics of the tested composition, to obtain a wavelength, at which each of the differential spectra reaches the zero value, as the reference wavelength for the tested composition.

Figure 4:
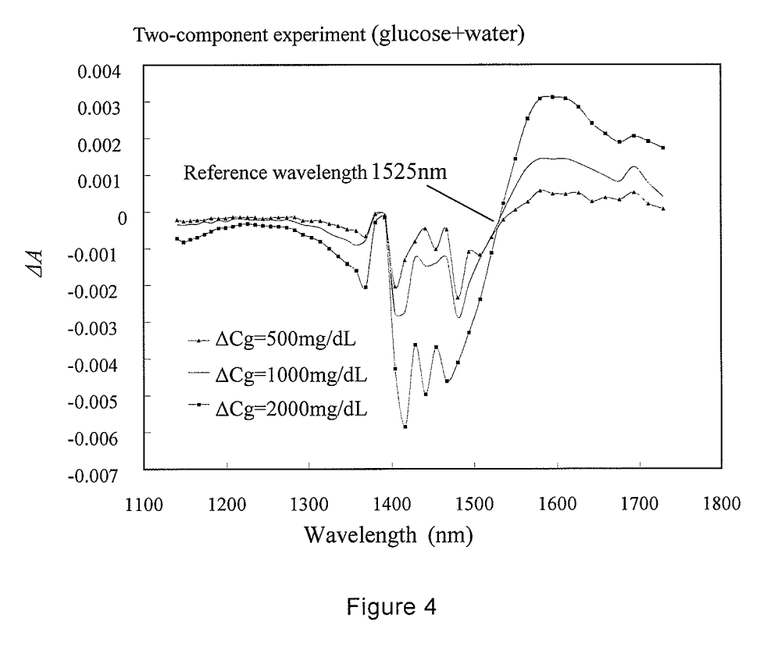
FIG. 4 is a graph showing the characteristic of a reference wavelength for the glucose in a two-component experiment.
Figure 5:
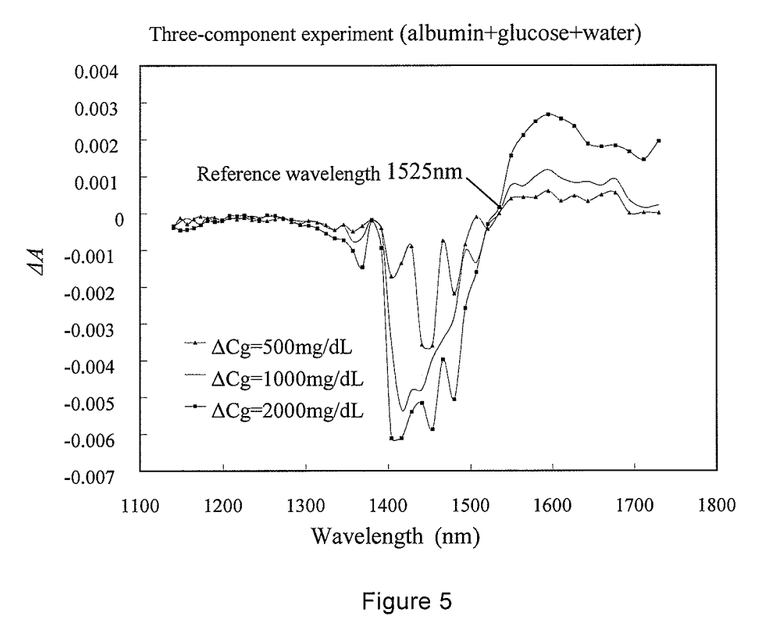
FIG. 5 is a graph showing the characteristic of a reference wavelength for the glucose in a three-component experiment.
Figure 6:
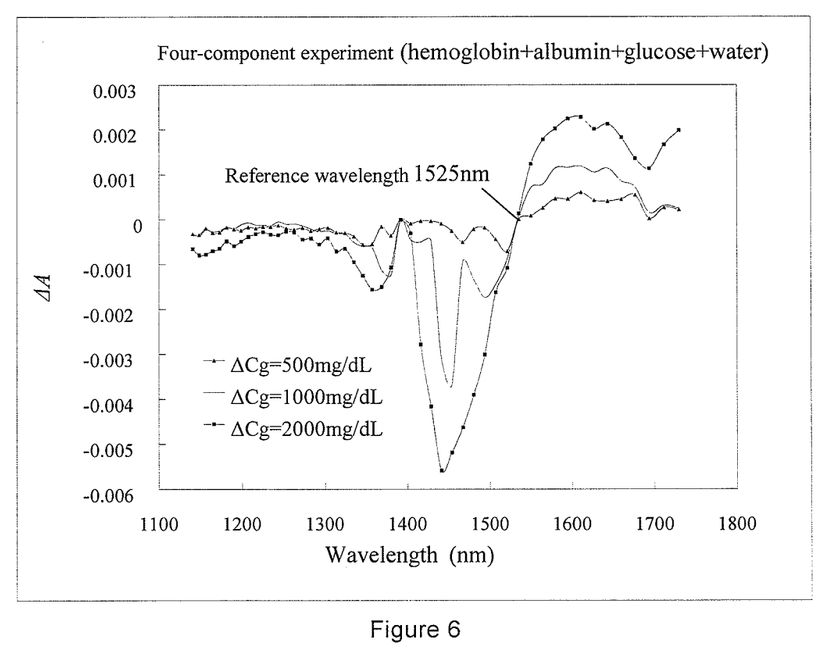
FIG. 6 is a graph showing the characteristic of a reference wavelength for the glucose in a four-component experiment.

Here, the existence characteristic of the reference wavelength is proved by a series of experiments ranging from easy to difficult, such as two-composition, three-composition and four-composition experiments. The results are shown in FIGS. 4, 5 and 6. The zero point of each differential absorbance curve in each experiment is at 1525 nm. That is, the reference wavelength for the aqueous glucose solution is 1525 nm.

Figure 7:
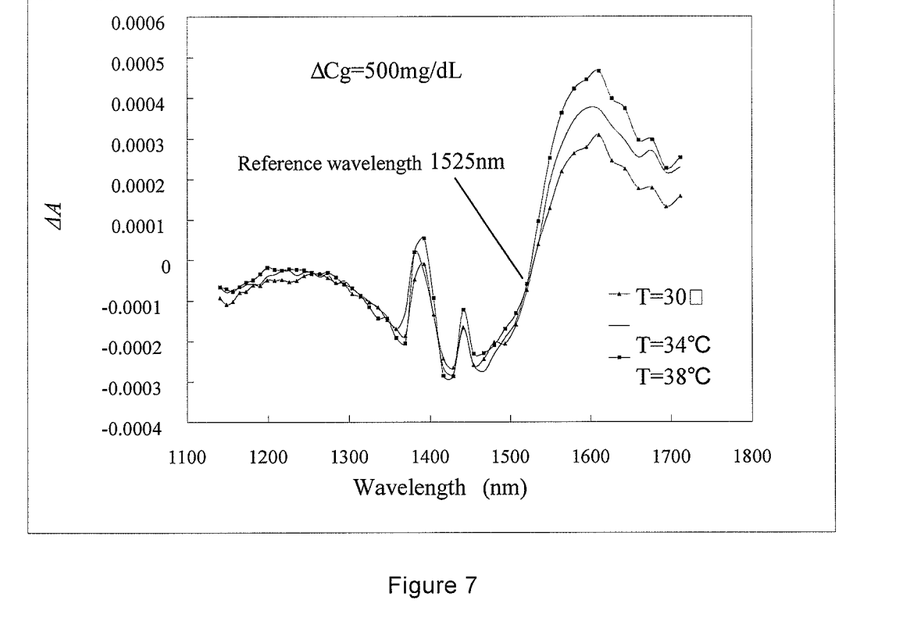
FIG. 7 is a graph showing the temperature characteristic of a reference wavelength for the aqueous glucose solution.

Moreover, the temperature characteristic of the reference wavelength position is analyzed based on the two-composition experiment of the aqueous glucose solution. The analysis is carried out with respect to the samples at different temperatures, such as 30° C., 34° C. and 38° C. As shown in FIG. 7, the zero point of each differential absorbance curve is the same, 1525 nm, at different temperatures. This means that the position of the reference wavelength for the aqueous glucose solution is independent of the temperature, and is constantly at the wavelength of 1525 nm.

Extracting Specific Signal of Tested Composition by Reference Wavelength Method

During the noninvasive and minimally invasive measurement of human body compositions, system drifts and background noises due to changes in other compositions and physiological state occur when the spectra are measured at different times, and thus will influence the measuring accuracy of the tested composition. According to an embodiment of the present invention, the spectral data are preprocessed by using the reference wavelength method, which brings effective interference cancellation. The key of the reference wavelength method is as follows: the value of the light intensity or absorbance measured at the reference wavelength is considered as a floating parameter, which reflects the interferences due to other factors than the tested composition in the sample and is independent of the concentration of the tested composition. Differential process is performed on the spectral signals at other wavelengths than the reference wavelength with respect to the spectral signals at the reference wavelength, so as to effectively reduce various noises as well as strengthen the extracted specific signal of the tested composition.

The output light intensity fully follows the Lambert-Beer Law under the circumstance of the pure absorption sample. It is assumed that the change of the concentration of the tested composition is $\Delta c$, a proportional shift of the input light intensity in the sample measurement with respect to that in the background measurement due to the drift of the light source or the interference of the environment is $\eta$, and there are concentration changes of other compositions during the measurement of the background and the sample. Then the received light intensities from the background and the sample can be given respectively by:

$$I_b(\lambda)=I_0(t_b,\lambda)\cdot\exp(-\mu_a\cdot l) \qquad (12)$$

$$I_s(\lambda)=I_0(t_b,\lambda)\cdot\eta\cdot\exp(-\mu_a\cdot l-\Delta\mu_{a\_\Delta c}\cdot l-\Delta\mu_{a\_\Delta other}\cdot l) \qquad (13)$$

where $I_b$ and $I_s$ are the received light intensities from the background and the sample respectively, and $I_0(t_b,\lambda)$ is the input light intensity during the background measurement, $\mu_a$ is the absorption coefficient of the background solution, $\Delta\mu_{a\_\Delta c}$ is the absorption coefficient change due to the concentration change of the sample $\Delta c$, $\Delta\mu_{a\_\Delta other}$ is the absorption coefficient change due to other factors, and l is the length of the light path.

Then the specific signal of the tested composition concentration can be given by:

$$A_G(\lambda)=-\mathrm{Ln}\frac{I_s(\lambda)}{I_b(\lambda)}+\mathrm{Ln}\eta-A_{other}(\lambda) \qquad (14)$$

where $A_G(\lambda)=\Delta\mu_{a\_\Delta c}(\lambda)\cdot l$, $A_{\Delta other}(\lambda)=\Delta\mu_{a\_\Delta other}(\lambda)\cdot l$.

The received light intensity is insensitive to the concentration change of the tested composition at the reference wavelength $\lambda_r$. Therefore, the light intensity change at $\lambda_r$ can be taken as the result of the background noise at the reference wavelength $\lambda_r$, and the absorbance change of the solution due to the concentration change of the tested composition is zero, i.e.

$$A_G(\lambda)=0 \qquad (15)$$

Then the background noise at the reference wavelength can be defined according to equations (14) and (15) as:

$$\mathrm{Ln}\eta-\Delta A_{\Delta other}(\lambda_r)=\mathrm{Ln}\frac{I_s(\lambda_r)}{I_b(\lambda_r)} \qquad (16)$$

When the concentration changes of the other compositions between the sample and the background are small, it can be approximately considered that $A_{\Delta other}(\lambda)\approx A_{\Delta other}(\lambda_r)$. Further, the specific signal of the tested composition extracted based on the reference wavelength under the circumstance of the pure absorption sample can be given by:

$$A_G(\lambda)=-\mathrm{Ln}\left(\frac{I_s(\lambda)}{I_b(\lambda)}\cdot\frac{I_b(\lambda_r)}{I_s(\lambda_r)}\right) \qquad (17)$$

For the complex scattering samples like human tissues, the effects of absorption and scattering should be taken into consideration together. According to the revised Lambert-Beer Law, considering the fluctuation of the input light intensity, the output light intensities of both the background and the sample with a certain concentration at a certain wavelength $\lambda$, are given respectively as:

$$I_b(\lambda) = I_0(t_b, \lambda) \cdot \exp(-\mu_{eff} \cdot l_{eff}) \quad (18)$$

$$I_s(\lambda) = I_0(t_b, \lambda) \cdot \eta \cdot \exp\left[-(\mu_{eff} + \Delta\mu_{eff-\Delta c}) \cdot l_{eff} \cdot (1 + K_{\Delta c})\right] \quad (19)$$

where $\mu_{eff}$ is the effective attenuation coefficient of the background, $\Delta\mu_{eff-\Delta c}$ is the effective attenuation coefficient change due to the concentration change of the tested composition $\Delta c$, $l_{eff}$ is the effective path of the scattering light passing through the sample, $K_{\Delta c}$ is the light path change ratio due to the concentration change of the scattering sample $\Delta c$.

According to equations (18) and (19), the specific signal of the tested composition can be given by:

$$A_G(\lambda) = \Delta\mu_{eff-\Delta c} \cdot l_{eff} \cdot (1 + K_{\Delta c}) \quad (20)$$

$$= \mathrm{Ln}\left(\frac{\eta \cdot I_b(\lambda)}{I_s(\lambda)}\right) + K_{\Delta c} \cdot \mathrm{Ln}\frac{I_b(\lambda)}{I_0(t_b, \lambda)}$$

Given the existence condition of the reference wavelength, it is $A_G(\lambda_r)=0$ at the reference wavelength $\lambda_r$, i.e.

$$\mathrm{Ln}\left(\frac{\eta \cdot I_b(\lambda_r)}{I_s(\lambda_r)}\right) + K_{\Delta c} \cdot \mathrm{Ln}\frac{I_b(\lambda_r)}{I_0(t_b, \lambda_r)} = 0 \quad (21)$$

According to equations (20) and (21), the specific signal of the tested composition under the circumstance of complex scattering like human tissues can be given by:

$$A_G(\lambda) = \mathrm{Ln}\frac{I_b(\lambda) \cdot I_s(\lambda_r)}{I_s(\lambda) \cdot I_b(\lambda_r)} + K_{\Delta c} \cdot \mathrm{Ln}\left(\frac{I_b(\lambda)}{I_b(\lambda_r)} \cdot \frac{I_0(t_b, \lambda_r)}{I_0(t_b, \lambda)}\right) \quad (22)$$

Based on the reference wavelength method according to the present invention, spectral signals of the background and the sample at the reference wavelength and the measuring wavelength can be measured respectively, and then the specific signal of the tested composition can be calculated by equation (17) or (22). Thus interferences due to background noises and system drifts can be effectively reduced, and the extracted specific signal of the tested composition can be strengthened. This method can be applied to the measurement of faint compositions like blood glucose concentration.

Temperature Correction of Spectrum

During the concentration measurement using the near-infrared spectroscopy, the fluctuation of the sample temperature can cause a big bias in the spectrum, which has a great influence on the measurement accuracy. According to an embodiment of the present invention, there is provided a temperature correction method based on the characteristic of the reference wavelength.

Taking the glucose measurement as an example, the replacement coefficient between the glucose and the water is defined as k, i.e.

$$\Delta c_w = k \cdot \Delta c_g \quad (23)$$

The replacement absorption coefficient of the aqueous glucose solution is given by:

$$\alpha_{total}(\lambda) = \alpha_g(\lambda) + k \cdot \alpha_w(\lambda) \quad (24)$$

In equations (2) and (24), $\alpha_w$, $\alpha_g$, $c_w$ and k are all dependent on the temperature.

Figure 8:
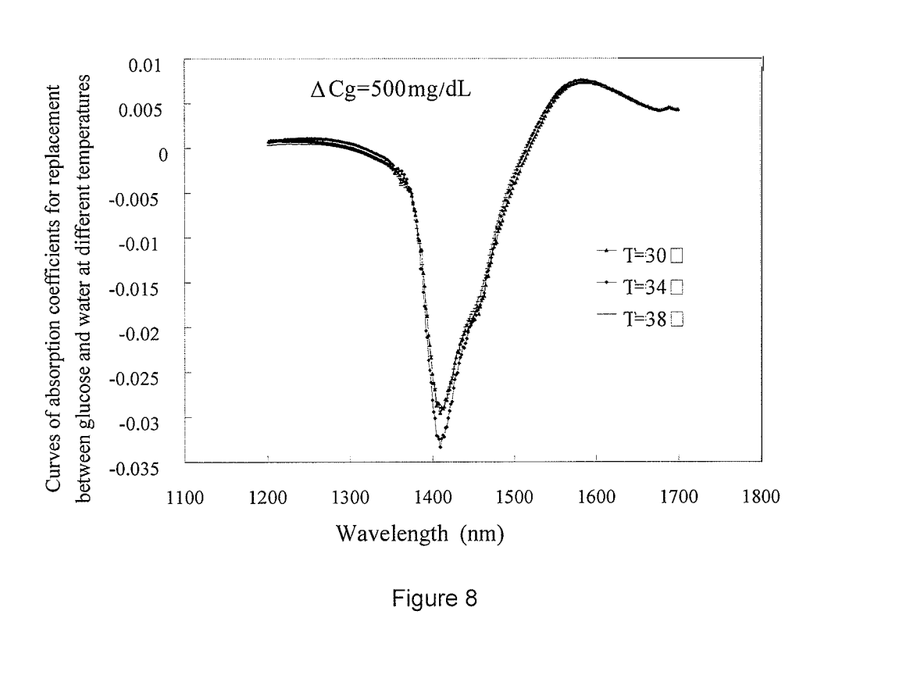
FIG. 8 is a graph showing curves of absorption coefficients for replacement between glucose and water at different temperatures.

The spectra of the aqueous glucose solution and the corresponding distilled water are obtained at different temperatures, so that the absorption coefficient of the aqueous glucose solution at different temperatures $\alpha_{total}^T(\lambda)$ can be calculated. As shown in FIG. 8, $\alpha_{total}^T(\lambda)$ is independent of the temperature.

Defining the temperature of the pure water as $T_1$, the temperature of the aqueous glucose solution as $T_2$, the difference between the absorbencies of those two is given by:

$$\Delta A(\lambda) = A_s^{T2}(\lambda) - A_b^{T1}(\lambda) = [\alpha_w^{T2}(\lambda) \cdot c_w^{T2} - \alpha_w^{T1}(\lambda) \cdot c_w^{T1}] \cdot l + \alpha_{total}(\lambda) \cdot \Delta c_g \cdot l \quad (25)$$

where $\Delta A_T(\lambda) = [\alpha_w^{T2}(\lambda) \cdot c_w^{T2} - \alpha_w^{T1}(\lambda) \cdot c_w^{T1}] \cdot l$, $\Delta A_G(\lambda) = \alpha_{total}(\lambda) \cdot \Delta c_g \cdot l$.

The difference in the absorbencies of the sample at different temperatures can be considered as the combination of difference in the absorbencies due to the temperature change and that due to the concentration change:

$$\Delta A(\lambda) = \Delta A_T(\lambda) + \Delta A_G(\lambda) \quad (26)$$

where $\Delta A_G(\lambda)$ is the glucose specific signal to be extracted, and $\Delta A_T(\lambda)$ is the interference signal due to the temperature change.

According to the definition of the reference wavelength, at the reference wavelength, $\Delta A_G(\lambda_r)=0$ and the following equation can be obtained:

$$\Delta A(\lambda_r) = \Delta A_T(\lambda_r) \quad (27)$$

The absorbency change at the reference wavelength is totally caused by the absorption coefficient change of the pure water due to the temperature change. So according to the absorbency change at the reference wavelength, the difference between the temperature in the aqueous glucose solution measurement and the temperature in the pure water measurement can be calculated.

The absorption coefficients and concentrations of the pure water at different temperatures can be obtained through experiments. Thus, when the temperatures of the sample and the background are calculated by using the reference wavelength method, the value of $\Delta A_T(\lambda)$ can be obtained. Then the specific signal of the glucose with the temperature interference cancelled is given by:

$$\Delta A_G(\lambda) = \Delta A(\lambda) - \Delta A_T(\lambda) \quad (28)$$

Figure 9:
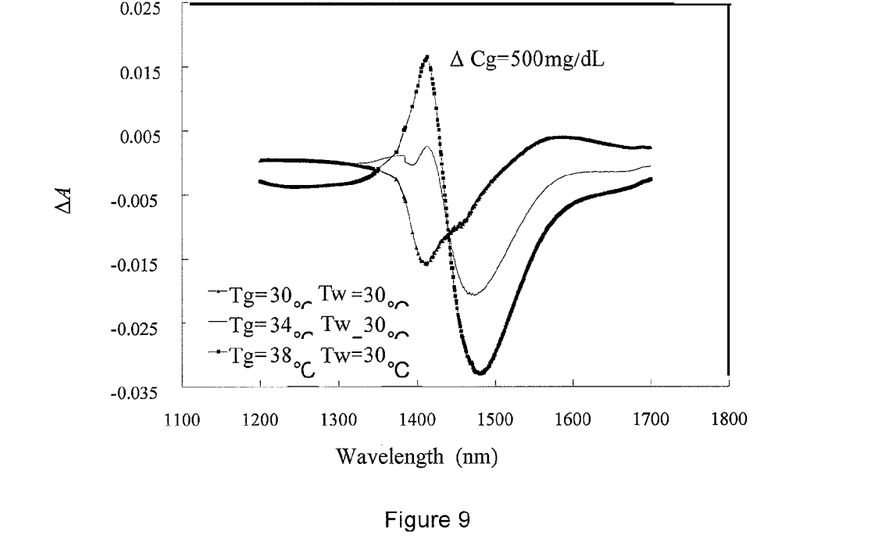
FIG. 9 is a graph showing a curve of absorbency difference signals in the glucose solution at different temperatures before the temperature correction (wherein Tg means the temperature at which the measurement is carried out with respect to the glucose solution; and Tw means the temperature at which the measurement is carried out with respect to the pure water as the background)
Figure 10:
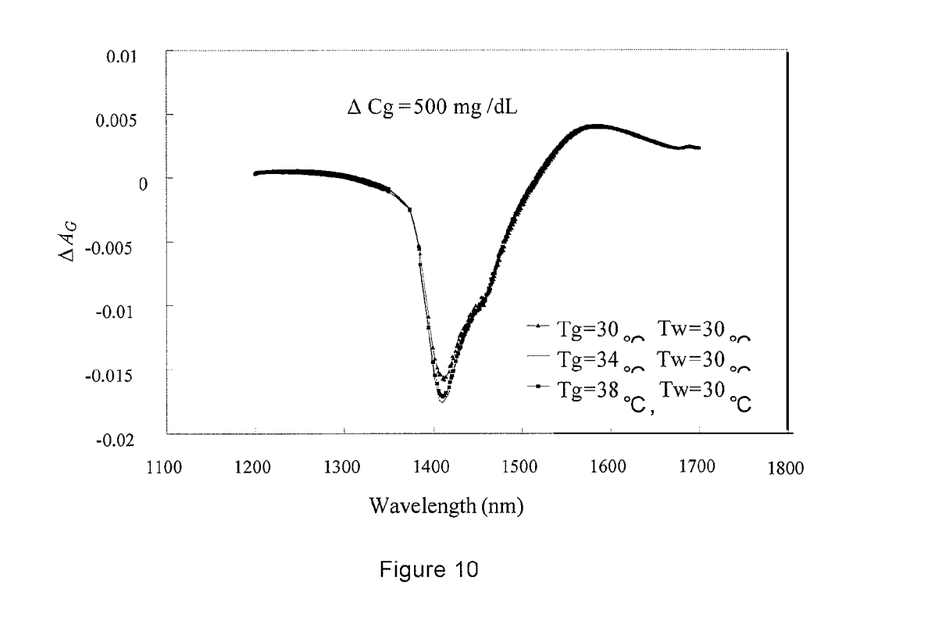
FIG. 10 is a graph showing a curve of characteristic signals of the glucose at different temperatures after the temperature correction (wherein Tg means the temperature at which the measurement is carried out with respect to the glucose solution; and Tw means the temperature at which the measurement is carried out with respect to the pure water as the background).

The temperature correction method may be verified through experiments as follows. The spectrum of the pure water is obtained at 30° C., and the spectra of the aqueous glucose solutions with the same concentration of 30 mg/dL are obtained at 30° C., 34° C. and 38° C. respectively. The difference in the absorbencies between the samples and the background is calculated by equation (25). As shown in FIG. 9, due to the temperature change, big differences exist in the absorbencies of the aqueous glucose solutions with the same concentration at different temperatures. If such spectra are used for the model analysis, the temperature interference is surely inevitable, which will influence the measurement accuracy of the glucose concentration. After a mathematical process of the spectra by using the temperature correction based on the reference wavelength method, as shown in FIG. 10, the spectra at different temperatures totally overlap with each other, and thus the characteristic spectral signal of the glucose can be obtained. So the temperature interference can be effectively cancelled and the accuracy of the near-infrared spectroscopy can be improved by using the temperature correction method based on the reference wavelength according to the present invention.

The above embodiments are provided just to illustrate the present invention, and are not intended to limit the present invention. The scope of the present invention is defined by the attached claims. Modifications and changes in forms and details to those embodiments are apparent to those skilled in the art, without departing from the principle and spirit of the present invention.

What is claimed is:

1. A method of detecting a concentration of a target component in a sample, including steps of:
   1) defining a wavelength at which a light intensity is insensitive to variation of the target component concentration as a reference wavelength for the target component;
   2) detecting spectra at the reference wavelength and a further measuring wavelength;
   3) processing the spectrum detected at the further measuring wavelength, with the spectrum detected at the reference wavelength as an inner reference, to obtain a characteristic spectrum including specific information of the target component;
   4) building a calibration model between the characteristic spectrum and the concentration of the target component; and
   5) determining the concentration of the target component based on the calibration model, wherein the reference wavelength $\lambda_r$ is defined as follows: for a pure absorption sample, $\alpha_g(\lambda_r)+\alpha_w(\lambda_r)\cdot k=0$; and for a scattering sample, $$\frac{6.44*10^{-5}*r^{2.37}*\rho_s*n_s*(n_s-n_w)^{1.09}}{\lambda_r^{0.37}*n_w^{3.09}} * \frac{1}{1-g(\lambda_r)} = \alpha_g(\lambda_r) + \alpha_w(\lambda_r)\cdot k,$$

wherein $\alpha_w$ and $\alpha_g$ are absorption coefficients of the water molecule and the target component molecule respectively, k is a replacement coefficient between the water and the target component, g is an anisotropic factor of the scattering sample, $n_s$ is a refractive index of scattering particles of the scattering sample, $n_w$ is the refractive index of the water, r is a radius of the scattering particles, $\rho_s$ is the number of scattering particles per unit volume of the sample ($nm^{-3}$).

2. The method according to claim 1, wherein the reference wavelength for the glucose in the aqueous glucose solution is 1525 nm.

3. The method according to claim 1, wherein a wavelength at which light intensity is most sensitive to the variation of the target component concentration is selected as the measuring wavelength.

4. The method according to claim 1, wherein in step 3), the specific information of the target component is obtained as follows:

for a pure absorption sample, the specific information including the variation of the target component concentration is:

$$A_G(\lambda) = -\text{Ln}\left(\frac{I_s(\lambda)}{I_b(\lambda)} \cdot \frac{I_b(\lambda_r)}{I_s(\lambda_r)}\right);$$

for a scattering sample, the specific information including the variation of the target component concentration is:

$$A_G(\lambda) = \text{Ln}\frac{I_b(\lambda)\cdot I_s(\lambda_r)}{I_s(\lambda)\cdot I_b(\lambda_r)} + K_{\Delta c}\cdot \text{Ln}\left(\frac{I_b(\lambda)}{I_b(\lambda_r)} \cdot \frac{I_0(t_b,\lambda_r)}{I_0(t_b,\lambda)}\right),$$

where $I_s(\lambda_r)$ and $I_b(\lambda_r)$ are intensities of the transmitted light from the sample and a background sample at the reference wavelength respectively, $I_s(\lambda)$ and $I_b(\lambda)$ are intensities of the transmitted light from the sample and the background sample at the measuring wavelength respectively, $I_0(t_b,\lambda_r)$ and $I_0(t_b,\lambda)$ are intensities of the light incident to the background sample at the reference wavelength and the measuring wavelength respectively, and $K_{\Delta c}$ is a percentage coefficient of the light path length variation caused by the concentration change of the target component of $\Delta c$.

5. The method according to claim 1, wherein the calibration model is built by the Partial Least Squares (PLS) method or the net analyte signal method.

* * * * *